US00RE36626E

United States Patent [19]

Henley

[11] E Patent Number: Re. 36,626

[45] Reissued Date of Patent: Mar. 28, 2000

[54] IONTOPHORETIC DRUG DELIVERY APPARATUS

[75] Inventor: Julian L. Henley, Guilford, Conn.

[73] Assignee: The APS Organization, LLP, Mass.

[21] Appl. No.: 09/119,200

[22] Filed: Jul. 20, 1998

Related U.S. Patent Documents

Reissue of:

[64] Patent No.: 5,160,316
Issued: Nov. 3, 1992
Appl. No.: 07/579,799
Filed: Sep. 10, 1990

[51] Int. Cl.[7] ..... A61N 1/30

[52] U.S. Cl. ..... 604/20; 607/148; 607/149; 607/152; 607/153

[58] Field of Search ..... 604/20; 607/148, 607/149, 152, 153

[56] References Cited

U.S. PATENT DOCUMENTS

| | | | |
|---|---|---|---|
| 2,047,308 | 7/1936 | Chapman | 607/152 |
| 3,848,600 | 11/1974 | Patrick, Jr. et al. | 607/153 |
| 4,211,222 | 7/1980 | Tapper | 607/153 |
| 4,416,274 | 11/1983 | Jacobsen et al. | 607/153 |
| 4,708,716 | 11/1987 | Sibalis | 604/20 |
| 4,763,660 | 8/1988 | Kroll et al. | 607/152 |
| 4,950,229 | 8/1990 | Sage, Jr. | 604/20 |

FOREIGN PATENT DOCUMENTS

| | | | |
|---|---|---|---|
| 8607269 | 12/1986 | WIPO | 604/20 |

*Primary Examiner*—Lee Cohen
*Attorney, Agent, or Firm*—Michael G. Petit

[57] ABSTRACT

Improved apparatus for the iontophoretic transdermal delivery of medication across the membrane formed by the body's skin is provided so the medication can be absorbed by the adjacent tissues and blood vessels. The improved apparatus is not reuseable and can be adapted for large dermal area application or for smaller sized area application, based on the specific electrode employed.

8 Claims, 5 Drawing Sheets

IONTOPHORETIC DRUG DELIVERY APPARATUS

Matter enclosed in heavy brackets [ ] appears in the original patent but forms no part of this reissue specification; matter printed in italics indicates the additions made by reissue.

BACKGROUND OF THE INVENTION

This invention relates generally to the electrokinetic mass transfer of medication transdermally and, more specifically, to improved apparatus for the iontophoretic delivery of medication across the membrane formed by the body's skin so the medication can be absorbed by the adjacent tissues and blood vessels.

Iontophoresis has existed for several centuries as a means of applying medication locally through a patient's skin and for delivering medicaments to the eyes and ears. The application of an electric field to the skin was found to greatly enhance the skin's permeability to various ionic agents. The use of iontophoretic techniques has obviated the need for hypodermic injection of medication and medicaments, thereby eliminating the concomitant problems of trauma, pain and risk of infection to the patient.

Iontophoresis involves the application of an electromotive force to drive or repel oppositely charged ions through the dermal layers into the area to be treated, either into the surrounding tissues for localized treatment or into the circulatory system for systemic treatment. Positively charged ions are driven into the skin at the anode while negatively charged ions are driven into the skin at the cathode. Studies have shown increased skin penetration of drugs at anodic or cathodic elelctrodes regardless of the predominant molecular ionic charge. This effect is mediated by polarization and osmotic effects. Regardless of the charge of the medicament employed, two electrodes are used in conjunction with the patient's skin to form a closed circuit to promote the penetration or absorption of the medicament on the working electrode.

More recently increased attention has been given to the use of iontophoresis to deliver drugs and other medicaments through a patient's skin to the desired treatment site. One readily observed benefit is the increased efficacy of the drugs delivered in this fashion. It has become desirable to produce encapsulations of unit doses in easily disposable, non-reusable applicators to be able to control the precise amount of medicament applied. However, an effective nonreusable applicator heretofore has not been available. A low cost, nonreuseable patient application electrode is essential in the treatment of contagious lesions, such as herpes, and helps to prevent further transmission of the disease.

In treating sensitive membranes, such as ear tissue, it is desirable to have an effective and safe way of delivering the medicament without risking harm to the tissue structure from direct electrical contact. It is also desirable to have a malleable or flexible electrode to adapt to each individual patient's ear canal shape and location of treatment. Such an applicator can be used to anaesthesize the tympanic membrane for a clinical myringotomy or for treating the skin in the ear canal.

It is also desireable to be able to treat large areas of the skin with medicament iontophoretically. Typical instances where this need arises is in the treatment of decubitis dermal ulcers or burns or other dermatological conditions, such as psoriasis, eczema or acne. An effective broad area iontophoretic treatment method can avoid more costly alternative treatments, avoid systemic toxicity or side effects, and dramatically increase therapeutic efficacy with lower dosage levels. However, such an applicator must employ an electrode that avoids current flowing along the path of least resistance into a lesion or skin rupture, resulting in a localized burn. This pattern of electrical current flow is also known as tunnelling. The concept of tunnelling combined with the introduction of multichannel electrodes driven by separate current isolated circuits has not been addressed by the prior iontophoretic devices.

These problems are solved in the design of the present invention by providing an improved iontophoretic mediacment applicator that is disposable and non-reusable. The improved iontophoretic applicator may also be suitable for treatment of large areas of skin or specific difficult to treat areas, such as the tympanic membrane.

SUMMARY OF THE INVENTION

It is an object of the present invention to provide an improved iontophoretic medicament applicator that can be used to treat a large dermal area.

It is another object of the present invention to provide an improved iontophoretic medicament applicator that can be used to effectively treat difficult to reach ear tissue.

It is still another object of the present invention to provide an improved iontophoretic medicament applicator that can be utilized for single dosage encapsulation and is disposable and non-reuseable.

It is a feature of the present invention that the iontophoretic medicament applicator for large dermal areas employs a multichannel electrodispersive matrix to drive the ionic medicament from the matrix or pad into the skin area.

It is another feature of the present invention that the iontophoretic medicament applicator for large dermal areas employs a carrier matrix with the medicament dispersed thereinto in combination with an adhesive layer to facilitate fastening to the patient's skin.

It is a further feature of the present invention that the iontophoretic medicament applicator for large dermal areas employs a conductive matrix and a carrier matrix with the medicament dispersed thereinto that are flexible to conform to the contours of the body area being treated.

It is still another feature of the present invention that the disposable iontophoretic medicament applicator employs an absorbent, inert material that is non-corrosive to contain the medicament or pharmaceutical agent.

It is yet another feature of the present invention that the disposable iontophoretic medicament applicator employs a nonreusable electrical contact that is destroyed after a single use.

It is yet another feature of the present invention that the disposable iontophoretic medicament applicator employs a color change indicator to show when the applicator has been used and its medicament depleted.

It is yet another feature of the present invention that the disposable iontophoretic medicament applicator for difficult to treat areas employs silastic tubing with two different diameters such that the larger diameter tubing serves to aspirate the medicament into the smaller diameter tubing which encases and extends beyond the metal electrode to protect the electrode from damage and prevent direct electrical contact with the patient's tissue.

It is an advantage of the present invention that the iontophoretic medicament applicator for large dermal areas improves the efficacy of topical agents and reduces the risk of harmful side effects that may occur with oral systemic treatment techniques.

It is another advantage of the present invention that the disposable iontophoretic medicament applicator for difficult to treat areas conducts the electrical current to the tissue through the solution into which the medicament is dissolved.

It is still another advantage of the present invention that the improved disposable iontophoretic medicament applicator has a low production cost, is safe to use and increases the efficacy of the medicament employed.

These and other objects, features and advantages are obtained by the improved iontophoretic medicament applicator of the present invention which can be used to treat large dermal areas, localized areas or small and difficult to reach areas.

BRIEF DESCRIPTION OF THE DRAWINGS

The objects, features and advantages of the invention will become apparent upon consideration of the following detailed disclosure of the invention, especially when it is taken in conjunction with the accompanying drawings wherein.

DETAILED DESCRIPTION OF THE PREFERRED EMBODIMENT

Figure 1:
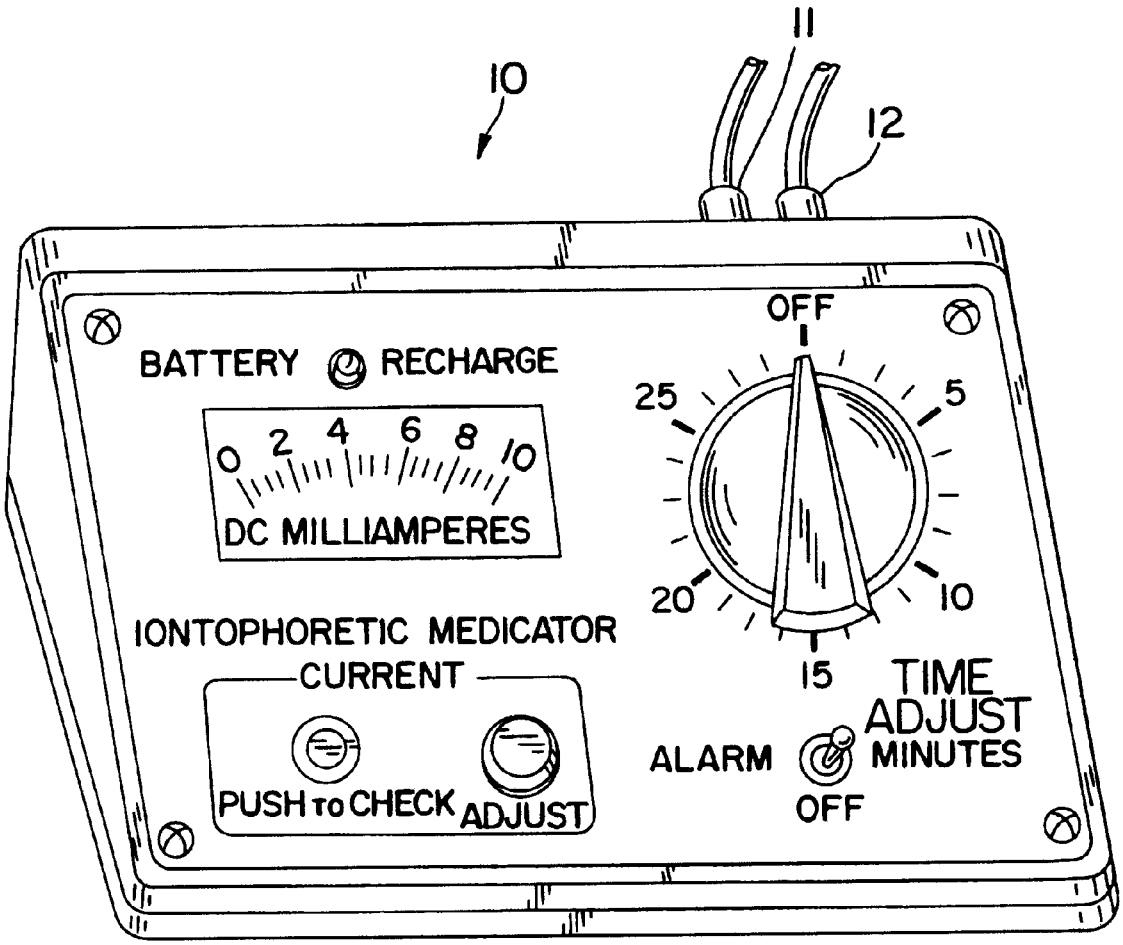
FIG. 1 is a front perspective view of the iontophoretic medicator electrical control to which the ground electrode and the improved iontophoretic applicator are connected.

FIG. 1 shows the control box for the iontophoretic drug delivery apparatus of the present invention. Control box, indicated generally by the numeral 10, is seen with a time adjustment dial to program the length of treatment, an alarm switch, a battery charge gauge for the rechargeable battery it contains, and a current check and adjustment control. The iontophoretic medicator has two electrode lead wires that lead from the positive electrode wire connection 11 and the negative wire electrode connection 12. These lead wires connect to two electrodes; one of which contains the ionic agent or medicament to be administered and the other which is the electric current distribution conductive member or grounding electrode.

Together these electrodes form a closed circuit through the patient's body when current is applied to promote the penetration or absorption of the ionic layer contained in the medicament of the working electrode. The polarity of the working electrode is selected based upon the polarity of the medicament to be administered. The working electrode will be described in greater detail hereafter. The current distributing electrode is usually a flexible sheet or film with a current distribution conductive member or layer, such as a metallic foil, for example aluminum or other suitable metals, a conductive rubber or resin film, carbon film or other conductive coating.

Figure 2:
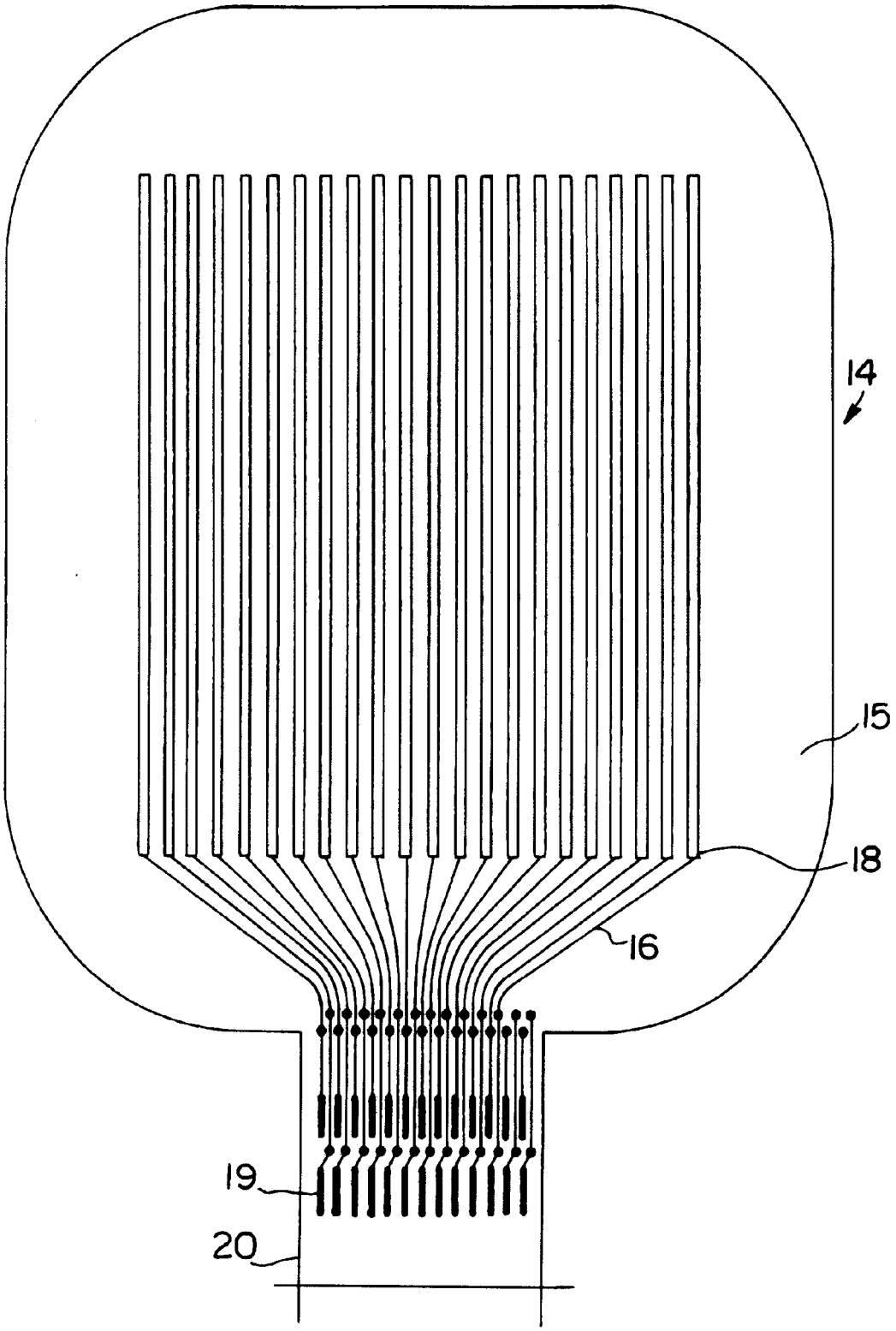
FIG. 2 is a top plan view of one potential embodiment of the improved multichannel iontophoretic applicator that can be used to treat large dermal areas.

FIG. 2 shows one embodiment of the iontophoretic applicator that is preferably disposable and non-reusable. Multichannel electrode is indicated generally by the numeral 14 and has a conductive matrix or pad 15 that is formed of a suitably electrodispersive material. Conductive matrix 15 is flexible so that it may be contoured to the body area on which it is placed and still cover a relatively wide area. Matrix 15 has a medicament carrying matrix 18 attached to it, such as by an adhesive. Carrying matrix 18 is formed from a porous material about ¼ of an inch thick that can be a honeycombed sponge-like material with vertical cells to minimize cross flow or lateral dispersion of the medicament that it contains. The grounding electrode (now shown) employed with the multichannel electrode 14 must also cover an area similarly large in size to the area covered by electrode 14.

A ribbon connector (not shown) connects the electrical power source to the electrode 14 and delivers the electrical current via the connectors 19 to the lead wires 16 that form the individual electrically conductive channels in the conductive matrix 15. The electrode folds over a rigid supporting substrate above the connectors 19, since the material of construction is flexible, to permit a good electrical connection to be made with the ribbon connector. Each channel preferably carries no more than 0.6 milliamps. The amount of current that flows to each channel is controlled by the control box 10 and its circuitry to prevent a tunneling effect from occurring. This prevents the flow of current along the path of least resistance through a lesion or skin rupture, for example, resulting in a burn to the patient at that location. The multichannel electrode 14 can employ a circuit pattern etched such as by laser or photoetching onto, for example, a Mylar® plastic with each channel isolated to obtain wide area dispersion. The connectors 19 scrape off upon removal from the ribbon connector power source to prevent reuse.

Each channel formed by the lead wires 16 can be electrically driven simultaneously or in a sequential multiplex fashion. The simultaneous or parallel electrical current use would be employed, for example, in the treatment or application of medicament to burns where a wide area dispersion is required. This type of an iontophoretic applicator will greatly improve the skin penetration by the medicament to actively deliver the treatment agent or medicament to either a wide regional area or to a specific lesion. It is effective also in the treatment of wide field dermatological conditions, such as eczema, psoriasis and acne. It is also effective for ionic retention of skin hydrating media to facilitate skin hydration in cosmetic applications and in dermal exfoliation to drive in medication to inflame the skin and cause the peeling of the external skin layer to stimulate reformation of collagen and collagen growth factors.

Figure 3:
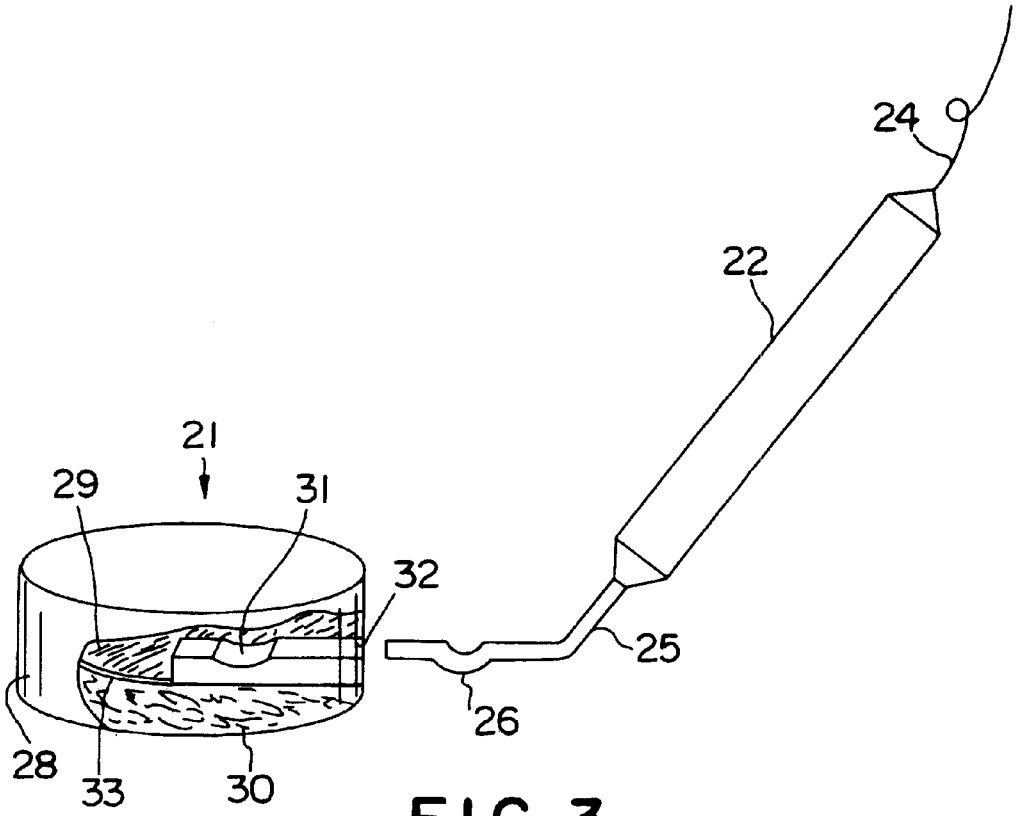
FIG. 3 is a side elevational view of a second potential embodiment of the improved disposable and non-reuseable iontophoretic applicator showing the reuseable applicator handle and the single use medicament dose unit.

FIG. 3 discloses a second embodiment of the improved disposable and non-reuseable iontophoretic applicator of the present invention, indicated generally by the numeral 21. An electrical lead wire 24 is shown connected to the connection handle 22 through which wire 24 passes. The handle 22 is removeably connected to the disposable iontophoretic applicator via the contact portion 25, which has a protruding portion 26 that serves as a scraper or electrical contact breaker upon removal from the disposable inontophoretic applicator through the electrode contact lead opening 32 in the packaging wall 28 of the disposable electrode or iontophoretic applicator. Upon insertion into the opening 32, the portion 26 makes electrical contact with the metal contact 31 that either contains a strippable conductive coating or is formed from an easily breakable material. The electrical current is conducted through the contact 31 to a metallic or other suitable conductive plate 33 to drive the medicament or treatment agent through the open-celled sponge-like material 30 through the patient's skin. The medicament or treatment agent is contained within a rupturable polymer reservoir 29 until time for treatment. A slight exertion of pressure or squeezing of the reservoir 29 releases the medicament or treatment agent into the open-celled sponge-like material for ionotophoretic direction into the patient's skin.

Upon removal of the contact portion 25 from the contact lead opening 32, the protruding portion 26 scrapingly strips the conductive metal coating from the metal contact 31 to prevent reuse of the disposable electrode 21. Electrode 21 is intentionally packaged with a single unit dose of treatment agent of medicament. The reservoir 29 can include a coloring agent, such as iodine, which turns dark blue upon contact with starch in the open-celled material 30 to visibly indicate that the unit dose encapsulation has been used. Other suitable coloring agents can include pH indicators, wet saturation indicators or oxidizable pigments.

The open-celled sponge-like material 30 should be inert to the medicament or treatment agent being employed, as well as being noncorrosive and stable with the treatment agent. Suitable materials include plastic pads, such as polyethylene, paper or cotton, porous ceramics, open-celled porous polytetrafluoroethylene, other inert plastics, and silicone rubber, such as may be employed with vertically aligned medicament-containing tubes. This material is also suitable for the carrying matrix 18 discussed above. A typical medicament that can be contained within the rupturable polymer is xylocaine.

The disposable electrode 21 possesses the advantages of not suffering from a leaching out of the medicament from the rupturable polymer reservoir, no attendant loss of efficacy, a long shelf life and little or no electrode corrosion.

Figure 4:
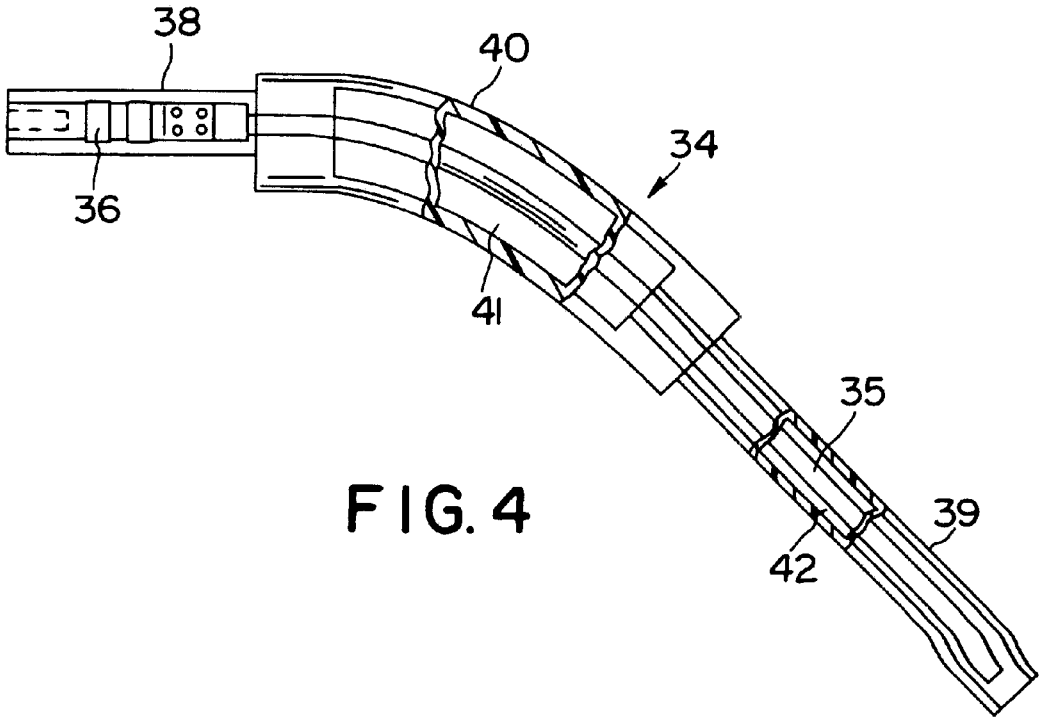
FIG. 4 is a side elevational view of a third potential embodiment of the improved iontophoretic applicator showing the dual diameter tubing surrounding the wire electrode and the medicament retaining space with a portion of the tubing cut away.

FIG. 4 shows the improved iontophoretic applicator used for treatment especially of the ear and the tympanic membrane, indicated generally by the numeral 34. The applicator or electrode 34 is malleable so that it can easily be formed to the desired shape. It includes a central electrode wire 35 that is connected to a wire connection 36 that connects to the appropriate lead wire from the control box 10 of FIG. 1. Electrode wire 35 is enclosed in a transparent plastic or silicone rubber tubing 39 to prevent direct electrical contact with the patient's skin in the inner area. Wire connection 36 is enclosed in an electrode wire connection covering 38 formed of the same material as the tubing 39. A cavity 41 surrounds the wire 35 beneath the electrode wire covering 40 and a similar cavity 42 surrounds the wire 35 beneath tubing 39 to permit medicament to be aspirated upwardly alongside wire electrode 35 into the cavity 41 by depressing or squeezing the covering 40. Releasing the covering 40 permits the medicament to run back down the wire 35 and exit the tubing 39 and be applied to the desired location requiring treatment.

The electrode wire connection can be any appropriate conductor material, such as silver or gold plated metal. The silastic tubing is made with two different diameters. The wide diameter in the central portion in conjunction with the cavity 41 serves to aspirate the medicament through the smaller diameter tubing 39 that protectively encases the wire electrode 35. This improved iontophoretic applicator has proven especially useful in clinical settings for anaesthesia of the tympanic membrane with, for example, a 4% by volume solution of xylocaine and a 2 part per thousand epinephrine. An electrical current of about 0.2 milliamps for about 90 seconds has provided satisfactory tympanic membrane anaesthesia to permit minor surgery without the need for further anaesthesia. It has also been effective for anaesthesizing the tympanic membrane for the common pediatric surgical procedure of performing a myringotomy for the placement of ventilation tubes within the ear.

Figure 5:
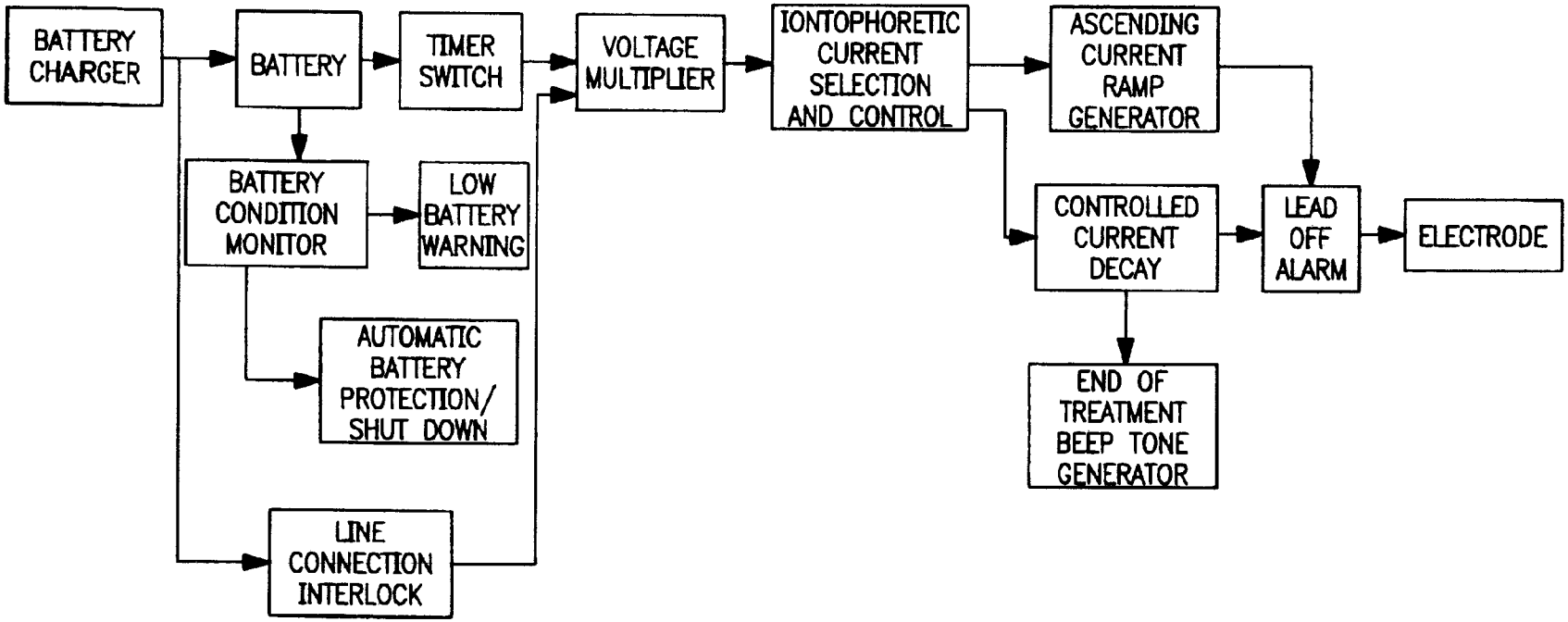
FIG. 5 is a block diagram of the iontophoretic medicator electrical control circuit used in conjunction with the second and third potential embodiments of the improved iontophoretic applicator.

FIG. 5 shows a block circuit diagram of the iontophoretic medicator electrical control circuit used in conjunction with the improved iontophoretic applicators of FIGS. 3 and 4. The control circuit and control box is equipped with a rechargeable battery and a battery charge monitor system to signal a low charge condition and to automatically shutdown the charging circuit to prevent overcharging. The line connection interlock is an electrical plug disconnect to prevent operation when charging.

The control box is provided with a timer switch to preset the length of iontophoretic treatment. Once the length of time has been selected a voltage multiplier is utilized to provide the current to iontophoretically drive the medicament into the patient's skin. The current selection and control is incrementally increased or changed to a controlled current level by depressing the iontophoretic medicator current push to check button and simultaneously depressing the adjust button of FIG. 1. to adjust the current level. In the current decay mode of operation, a beeping tone occurs at the end of the selected time period to indicate the end of the treatment period. Simultaneously, electrical current to the electrode is gradually terminated in a ramping down of the current to the patient to avoid abrupt change. An alarm override for disconnection of the alarm is available under both modes of operation, such as by means of the toggle switch seen in FIG. 1.

Figure 6:
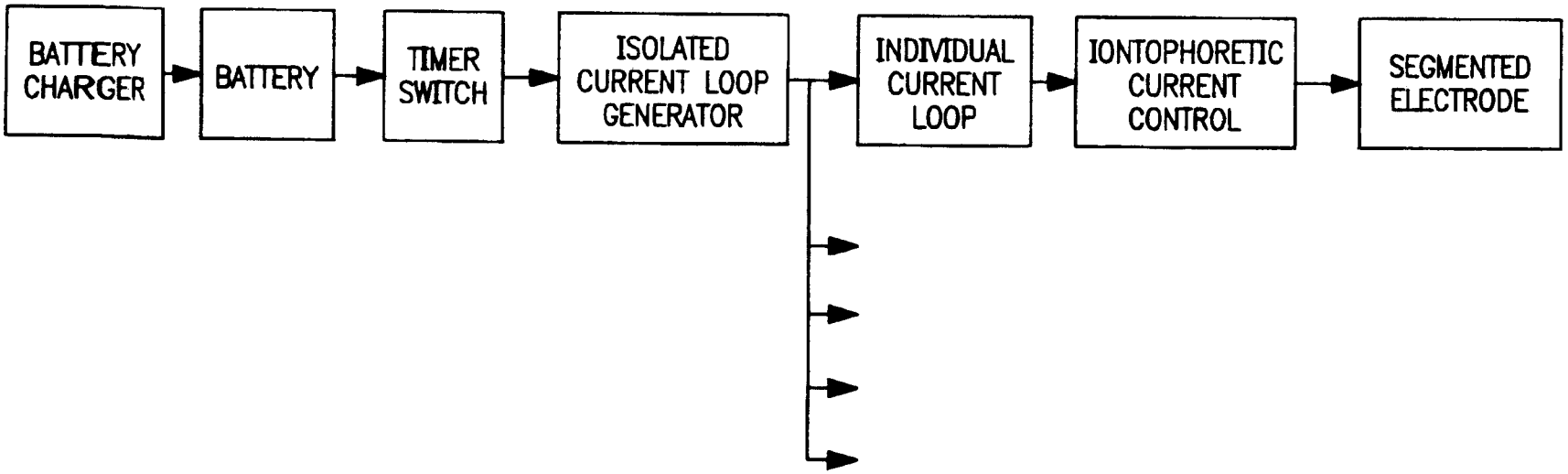
FIG. 6 is a block circuit diagram of the iontophoretic medicator electrical control circuit used in conjunction with the first large dermal area embodiment of the improved iontophoretic applicator.

FIG. 6 shows the block circuit diagram of the large area iontophoretic medicator control circuit employed with the multichannel iontophoretic applicator of FIG. 2. This control circuit also employs a rechargeable battery and timer switch to select the desired length of treatment. An isolated current loop generator is employed to feed current to the individual channels in the multichannel electrode via the plurality of individual current loops. Each current loop drives one band or channel in the multichannel electrode. It has been found that 0.6 milliamps current flowing to each channel in use within a wide field dispersion grounding electrode such as that seen in FIG. 2 provides a safe operation level of the iontophoretic device and avoids the tunnelling effect of current flowing along the path at least resistance and concentrating in, for example, a lesion or skin rupture, resulting in a burn to the patient. This permits current to be distributed over the large area of the multichannel electrode and drive medicament through a patient's skin over a large dermal area. However, depending upon the electrode configuration, this current level can vary from about 0.1 to about 1.2 milliamps.

While the invention has been described above with references to specific embodiments thereof, it is apparent that many changes, modifications and variations in the materials, arrangements of parts and steps can be made without departing from the inventive concept disclosed herein. For example, in employing the multichannel iontophoretic electrode of the present invention, it is possible to employ a biofeedback control of its operation to release, for example, more cardiovascular medication during periods of increased physiological demands, such as exercise or angina attack by linking the penetration of nitroglycerine with heart rate, the physiological indicator of oxygen demand by the heart. In the latter instance, the electrode would measure the increased demand to stimulate more delivery of the transdermal medication, in this case, nitroglycerine such as that commercially available under the tradename Nitropaste. This type of a biofeedback system is an active system for a percutaneous nitroglycerine delivery system that is an improvement over existing passive percutaneous delivery systems. Alternate applications also exist in hormonal therapy, for example in the administration of insulin or steroids based on blood sugar levels and dinurnal cycles, as appropriate. The large area multichannel electrode shown in FIG. 2 can also be adapted for use in dental anaesthesia in the form of a bite block, burn treatment and for the treatment of baldness, such as by the transdermal administration of Minoxidal®. Additionally, a conductive gel can also be used to impregnate the porous medicament carrying medium to increase the physical stability and the tissue adhering characteristics of the electrode.

Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. An improved iontophoretic medicament applicator for use with an electrically isolated electrical current loop generator and contactable with a patient's skin that is to be penetrated by the medicament, comprising in combination:

(a) a medicament carrying medium;

(b) an electrically conductive means for conducting electrical current connected to the medicament carrying medium, the electrically conductive means including a [plurality of] multichannel [electrodes] *electrode*, each electrode channel being electrically driven in a current isolated fashion through a corresponding plurality of individual current loops with each channel receiving the same current level to iontophoretically drive the medicament through the patient's skin in a wide area distribution without incurring an electrical current tunneling effect.

2. The iontophoretic medicament applicator of claim 1 wherein the electrically conducive means further is supported by a flexible plastic material.

3. The iontophoretic medicament applicator of claim 2 wherein the [plurality of] multichannel [electrodes] *electrode* supported by the flexible plastic material further comprises a circuit pattern etched onto the flexible plastic material.

4. The iontophoretic medicament applicator of claim 3 wherein the circuit pattern further comprises multiple electrically conductive channels that are electrically driven simultaneously or in a sequential multiplex fashion.

5. The iontophoretic medicament applicator of claim 2 wherein the medicament carrying medium further comprises a porous material or a conductive gel.

6. The iontophoretic medicament applicator of claim 5 wherein the porous medicament carrying medium further comprises a sponge-like material with vertical cells.

7. The iontophoretic medicament applicator of claim 6 wherein the porous medicament carrying medium further is selected from the group consisting of polyethylene, paper, cotton, ceramic, silicon rubber and polytetrafluoroethylene.

8. The iontophoretic medicament applicator of claim 1 wherein the electrically conductive means further include connectors which are adapted to be connected to the electrically isolated current loop generator and to each of the plurality of individual current loops, the electrical connectors having a conductive coating that is removable upon disconnection from the electrical current loop generator to prevent reuse by breaking the electrical flow path.

* * * * *